United States Patent [19]

Barden et al.

[11] Patent Number: 5,055,486

[45] Date of Patent: Oct. 8, 1991

[54] 13-ALKYL-23-IMINO DERIVATIVE OF LL-F28249 COMPOUNDS AND THEIR USE AS ENDO- AND ECTOPARASITICIDAL, INSECTICIDAL, ACARICIDAL AND NEMATOCIDAL AGENTS

[75] Inventors: Timothy C. Barden, Cranbury, N.J.; Brian L. Buckwalter, Yardley, Pa.

[73] Assignee: American Cyanamid Company, Stamford, Conn.

[21] Appl. No.: 455,686

[22] Filed: Dec. 22, 1989

[51] Int. Cl.$^5$ .................. A61K 31/335; C07D 313/06
[52] U.S. Cl. ..................................... 514/450; 549/264
[58] Field of Search ........................ 549/264; 514/450

[56] References Cited

U.S. PATENT DOCUMENTS 4,857,509 8/1989 Frei et al. .............................. 549/264
4,916,154 4/1990 Asato et al. .......................... 549/264

FOREIGN PATENT DOCUMENTS 2176182 12/1986 United Kingdom ................ 549/264

*Primary Examiner*—Richard L. Raymond
*Assistant Examiner*—M. W. Russell

[57] ABSTRACT

There are provided certain 13-alkyl-23-imino-LL-F28249 compounds which are useful for controlling endo- and ectoparasites, insects, acarids and nematodes.

9 Claims, No Drawings

13-ALKYL-23-IMINO DERIVATIVE OF LL-F28249 COMPOUNDS AND THEIR USE AS ENDO- AND ECTOPARASITICIDAL, INSECTICIDAL, ACARICIDAL AND NEMATOCIDAL AGENTS

SUMMARY OF THE INVENTION

The present invention relates to certain 13-alkyl-23-imino-LL-F28249 compounds. These compounds are effective for controlling endo- and ectoparasites and may be used to protect warm-blooded animals against infestation and infection by endo- and ectoparasites. The compounds may also be applied to a wide variety of agronomic crops and the surroundings in which said crops are grown or growing to protect said crops from the damage caused by insects, acarids and nematodes.

The designation LL-F28249 is used to describe compounds produced by the fermentation broth of *Streptomyces cyaneogriseus* subspecies *noncyanogenus* deposited in the NRRL collection under deposit accession No. 15773. The morphological characteristics of said compounds and methods for the production thereof are described in U.S. Pat. application Ser. No. 732,252, filed on May 10, 1985, which is a continuation-in-part of U.S. Pat. application Ser. No. 617,650, filed Jun. 5, 1984. These patent applications are incorporated herein by reference thereto.

DESCRIPTION OF THE PREFERRED EMBODIMENTS

The compounds of the invention have the structural formula:

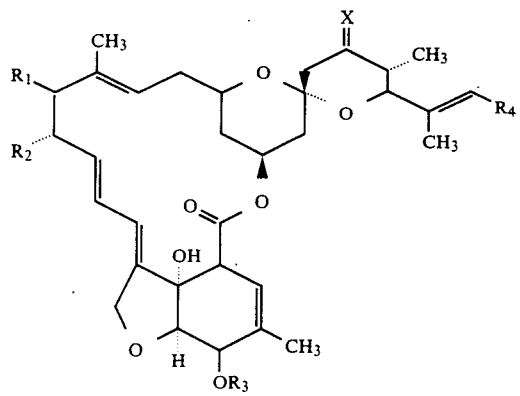

(I)

wherein $R_1$ is $C_1$-$C_4$ alkyl;
$R_2$ is hydrogen, methyl or ethyl;
$R_3$ is hydrogen, $C_1$-$C_4$ alkyl or

$R_5$ is hydrogen, $C_1$-$C_4$ alkyl, $C_1$-$C_4$ haloalkyl, $C_1$-$C_4$ alkoxy, phenoxy, $C_1$-$C_4$ alkoxymethyl, phenoxymethyl, or phenyl optionally substituted with 1 nitro, 1-3 halogens, 1-3 $C_1$-$C_4$ alkyl, or 1-3 $C_1$-$C_4$ alkoxy groups;
$R_4$ is methyl, ethyl or isopropyl;
$R_6$ is hydrogen, $C_1$-$C_4$ alkyl, $C_1$-$C_4$ alkoxymethyl, $C_1$-$C_4$ alkanoyl, benzyl or phenyl;
X is oxygen, $NOR_6$ or $NNHR_7$;

$R_7$ is $C_1$-$C_4$ acyl, $C_1$-$C_4$ alkyl or benzoyl.

A preferred group of 13-alkyl-23-imino-LL-F28249 compounds have the structural formula shown above wherein
$R_1$ is methyl, ethyl or isopropyl;
$R_2$ is methyl;
$R_3$ is hydrogen, $C_1$-$C_4$ alkyl, or

$R_5$ is hydrogen, $C_1$-$C_4$ alkoxymethyl, $C_1$-$C_4$ halomethyl or formyl;
$R_4$ is isopropyl;
X is $NOR_6$; and
$R_6$ is $C_1$-$C_4$ alkyl.

The compounds may be represented by the following structural formula:

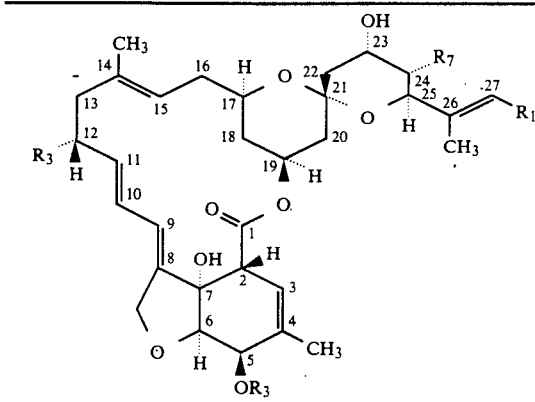

| Component | $R_1$ | $R_2$ | $R_3$ | $R_7$ |
|---|---|---|---|---|
| LL-F28249α | CH(CH$_3$)$_2$ | H | CH$_3$ | CH$_3$ |
| LL-F28249β | CH$_3$ | H | CH$_3$ | CH$_3$ |
| LL-F28249γ | CH$_3$ | CH$_3$ | CH$_3$ | CH$_3$ |
| LL-F28249ε | CH(CH$_3$)$_2$ | H | H | CH$_3$ |
| LL-F28249ζ | CH$_2$CH$_3$ | H | CH$_3$ | CH$_3$ |
| LL-F28249θ | CH(CH$_3$)$_2$ | H | CH$_3$ | CH$_2$CH$_3$ |
| LL-F28249ι | CH(CH$_3$)$_2$ | H | CH$_2$CH$_3$ | CH$_3$ |
| LL-F28249λ | CH(CH$_3$)$_2$ | CH$_3$ | CH$_3$ | CH$_3$ |

Surprisingly, it has been found that chemical modification at the 5, 13 and 23 positions of the compounds shown above enhances the endo- and ectoparasiticidal, insecticidal, acaricidal and nematocidal activity of said compounds. More particularly, the 13-alkyl-23-imino derivatives of 5-hydroxy and 5-O-substituted-LL-F28249 compounds demonstrate potent endectocidal and insecticidal activity.

The compounds of the present invention may be prepared by reacting LL-F28249 compounds with acetic anhydride to yield the 5-acetoxy-F28249 compound (II). Reacting the 5-acetoxy-LL-F28249 compound with calcium carbonate and methyl oxalyl chloride followed by treatment with hydrochloric acid yields the 5-acetoxy-23-{[(methoxycarbonyl)-carbonyl]oxy}-LL-F28249 compound (III). The thus-obtained compound (III) is converted to the 5-acetoxy-13β-hydroxy-23-{[(methoxy carbonyl)carbonyl]oxy}-LL-F28249 (IV) by treatment with formic acid and selenium dioxide followed by reaction with hydrochloric acid. Reacting the formula (IV) compound with ethyl chloroformate, pyridine and 4-dimethylaminopyridine yields the 5-acetoxy-13β-[(ethoxycarbonyl)oxy]-23-{[(methoxycarbonyl)carbonyl]oxy}-LL-F28249 compound (V). Reacting the said formula (V) compound with trialkylaluminum yields a 5-acetoxy-13β-alkyl-LL-F28249 compound (VI). The formula (VI) compound is converted to a 5-acetoxy-13β-alkyl-23-oxo-LL-F28249 compound (VII) by treatment with 4-methylmorpholine N-oxide and tetrapropyl ammonium perruthenate and then reacted with an alkoxylamine hydrochloride to yield a 5-acetoxy-13β-alkyl-23-(O-alkyloxime)-LL-F28249 compound (VIII). Reacting compound (VIII) with a strong base, such as sodium hydroxide, yields a desired formula (I) 13β-alkyl-23-(O-alkyloxime)-LL-F28249 compound. This reaction scheme is illustrated in flow diagram I:

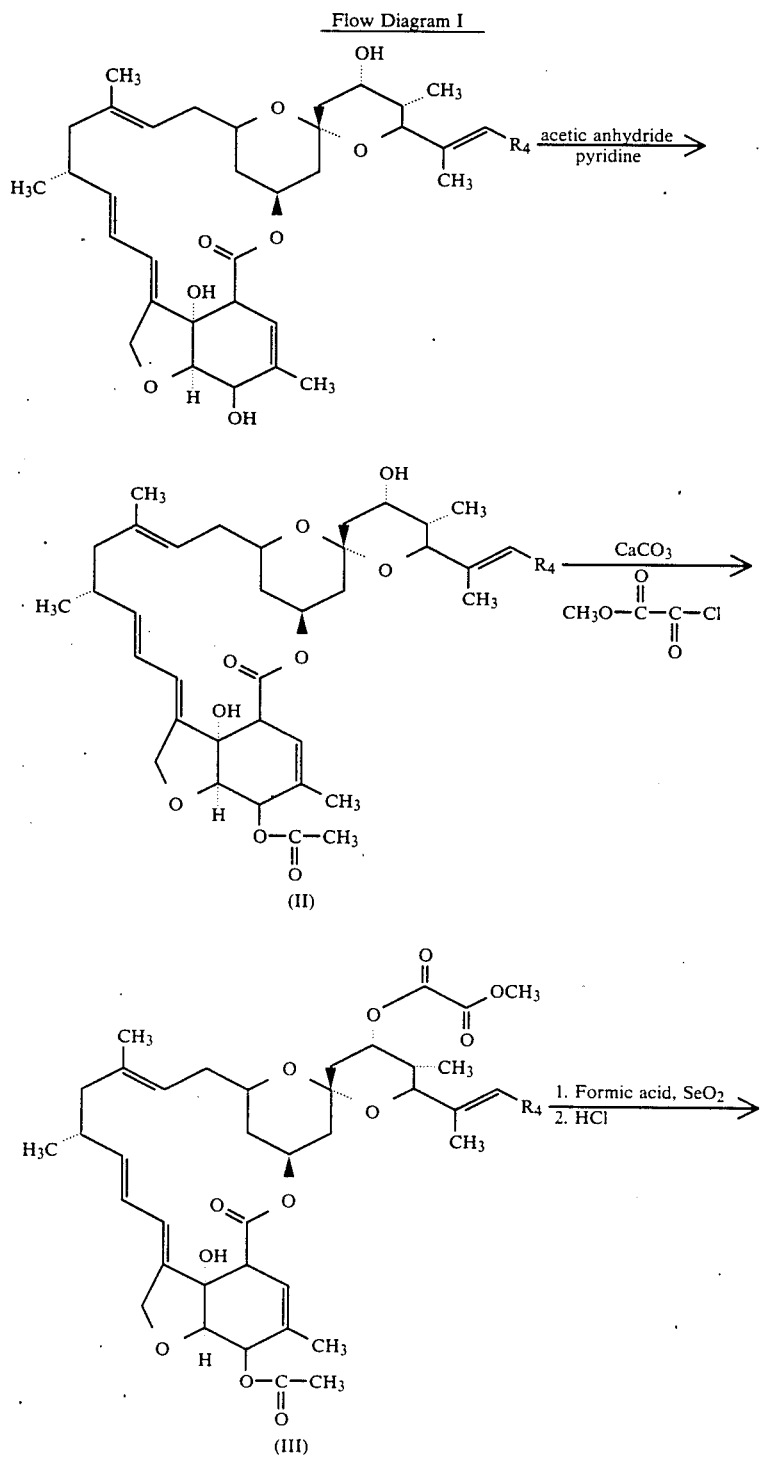

-continued
Flow Diagram I
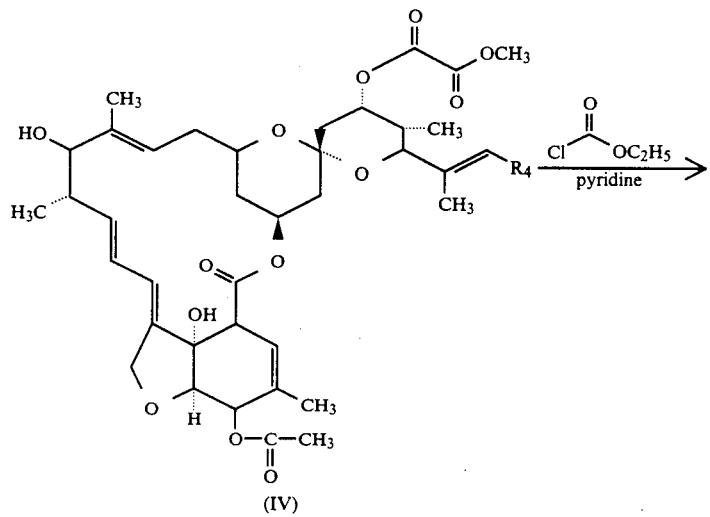
(IV)
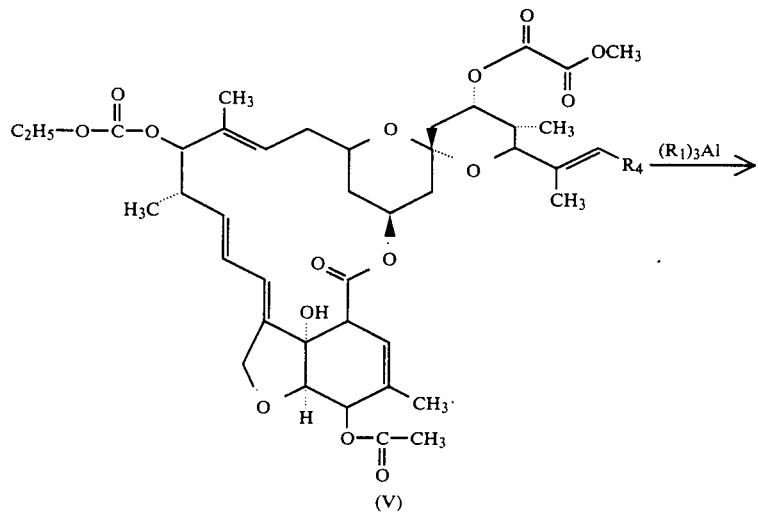
(V)
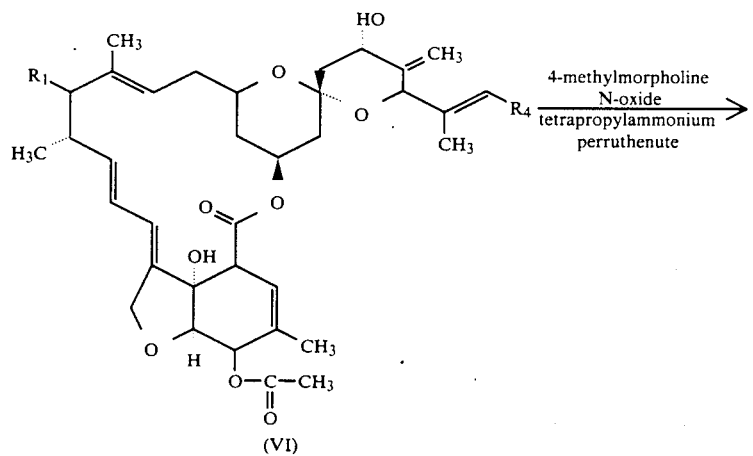
(VI)

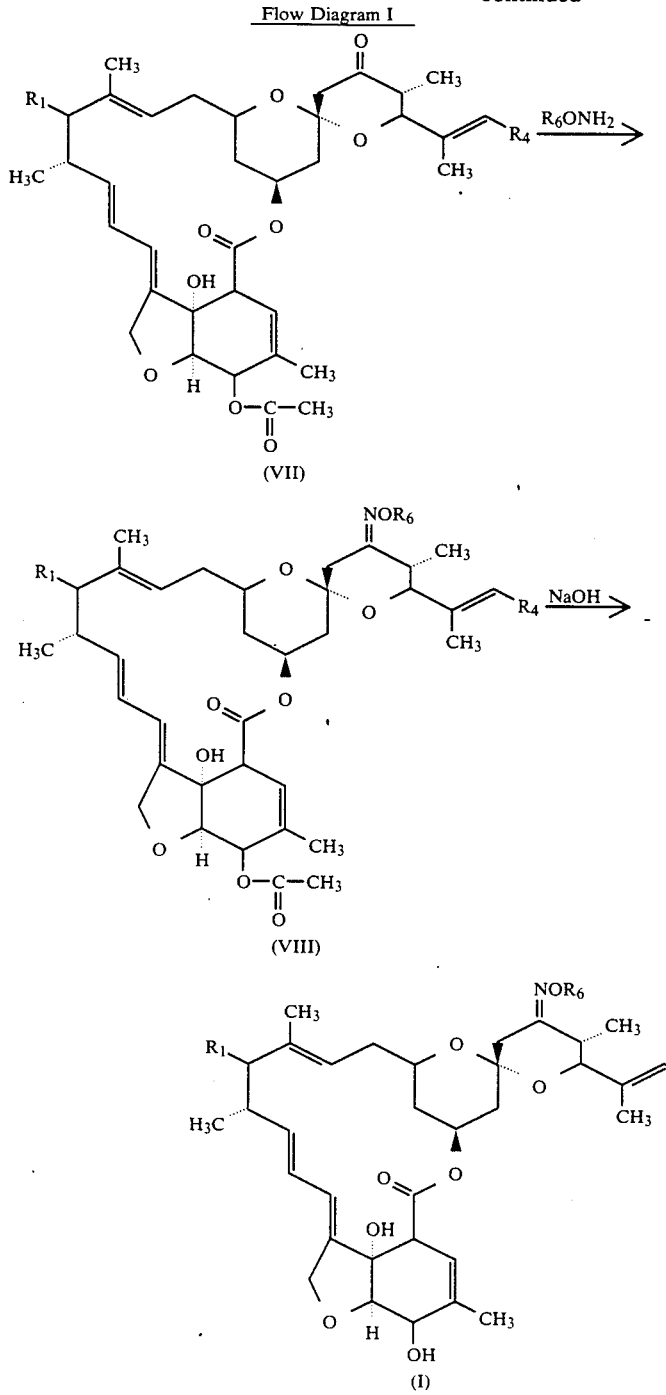

It has been found that the compounds of the invention are effective for treating, controlling and protecting a warm-blooded animal from infestation and infection by endoparasites, such as helminths, and ectoparasites, such as mites, ticks, lice, fleas and other biting insects in domesticated animals and poultry.

For use in the treatment of warm-blooded animals such as cattle, sheep, swine, horses, dogs or other farm or companion animals the compounds of the invention may be administered orally in a dosage unit form such as a capsule, bolus or tablet, or as a liquid drench. The drench is normally a solution, suspension or dispersion of the active ingredient usually in water together with a suspending agent such as bentonite and a wetting agent or like excipient and an antifoaming agent. Drench formulations generally contain about 0.001 to 0.5% by weight of the active compound. The capsules and boluses comprise the active ingredient admixed with a carrier vehicle such as starch, talc, magnesium stearate or di-calcium phosphate.

Where it is desired to administer the LL-F28249 derivatives in a dry, solid dosage unit form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such dosage unit formulations may be varied widely with respect to their total weight and content of the parasiticidal agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the parasiticidal compounds of the invention may be administered to animals parenterally, for example, by intraruminal, intramuscular, intratracheal or by subcutaneous injection, in which event the active ingredient is dissolved or dispersed in a liquid carrier vehicle. For parenteral administration, the active material is admixed with an acceptable vehicle, preferably a vegetable oil such as peanut oil, cotton seed oil or the like. Other parenteral vehicles such as organic preparations using solketal, propylene glycol, glycerol formal and aqueous parenteral compositions may also be used in the preparation of parenteral formulations for administration to warm-blooded animals.

In these formulations the active compound or compounds are dissolved or suspended in the formulation in sufficient amount to provide about 0.005 to 5% by weight of the compound.

It has also been found that the compounds of the invention exhibit surprising insecticidal, nematicidal and acaricidal properties, making them useful for controlling insects, nematodes and acarids and protecting agronomic crops, trees, shrubs, stored grain and ornamental plants from damage caused by insects, nematodes and acarids.

For plant application, the compounds of the invention may be formulated into dry compacted granules, flowable compositions, wettable powders, dusts, dust concentrates, microemulsions and the like, all of which lend themselves to soil, water and/or foliage application and provide the requisite plant protection. Such compositions include the compounds of the invention admixed with agronomically acceptable solid or liquid carriers.

In these compositions the compounds are intimately mixed or ground together with the composition in sufficient amounts to provide about 3 to 20% by weight of the active compound in said composition. The compositions may be applied using known techniques such as sprays, dusts, emulsions, wettable powders, flowables and the like to the growing or stored crops to provide protection against infestation by agricultural pests.

In order to facilitate a further understanding of the invention, the following examples are presented primarily for the purpose of illustrating certain more specific details thereof. The invention is not to be limited thereby except as defined in the claims. Unless otherwise noted, all parts are by weight.

EXAMPLE 1

Preparation of 5-Acetoxy-LL-F28249α

To a 0° C. solution of LL-F28249α(32.57 g), 39.3 mmol) and pyridine (200 mL) is added acetic anhydride (20 mL, 212 mmol). The reaction mixture is stirred for 3 days at 0° C. Concentration in vacuo of the reaction mixture yields a yellow residue. The residue is dissolved into ethyl acetate, washed sequentially with water, dilute hydrochloric acid solution, water, 10% sodium bicarbonate solution and brine, dried over anhydrous sodium sulfate and concentrated in vacuo to yield the title compound as a pale yellow foam (35.47 g), identified by NMR spectral analyses.

EXAMPLE 2

Preparation of 5-Acetoxy-23-{[(methoxycarbonyl)carbonyl]oxy}-LL-F28249α

To a mixture of 5-acetoxy-LL-F28249α (35.47 g, 53.1 mmol), calcium carbonate (11.04 g, 110.3 mmol) and methylene chloride is added methyl oxalyl chloride (8.0 mL, 87 mmol). The reaction mixture is stirred for hours at room temperature. The reaction mixture is then cooled to 0° C. and 2 normal hydrochloric acid solution (60 mL) is added slowly to the mixture. Water is added to the mixture and the layers are separated. The organic layer is diluted with methylene chloride, washed sequentially with water, 10% sodium bicarbonate solution, water and brine, dried over anhydrous sodium sulfate and concentrated in vacuo to yield the title compound as a yellow foam (41.28 g), identified by NMR spectral analyses.

EXAMPLE 3

Preparation of 5-Acetoxy-13β-hydroxy-23-{[(methoxycarbonyl)carbonyl]oxy}-LL-F28249α

To a mixture of 5-acetoxy-23-{[(methoxycarbonyl)carbonyl)carbonyl]oxy}-LL-F28249α (41.28 g, 55.71 mmol) and 88% formic acid solution (200 mL) is added selenium dioxide (8.6 g, 77.5 mmol). The reaction mixture is stirred at room temperature for 90 minutes then the mixture is diluted with ethyl acetate and filtered through diatomaceous earth. The filtrate is cooled in an ice/acetone bath. 20% sodium hydroxide solution (550 mL) is then added slowly with stirring to the cold filtrate. The organic layer is separated and washed sequentially with 10% sodium bicarbonate solution, water and brine, dried over anhydrous sodium sulfate and concentrated in vacuo to yield an orange foam. The foam is dissolved into methanol and 2 normal hydrochloric acid solution (25 mL) is added. The reaction mixture is stirred at room temperature for 2 ½ hours, then 10% sodium bicarbonate solution (30 mL) is added. Concentration of the mixture in vacuo yields a dark red residue. The red residue is dissolved into ethyl acetate, washed sequentially with water, 10% sodium bicarbonate solution and brine, dried over anhydrous sodium sulfate and concentrated in vacuo to yield an orange foam. The foam is chromatographed using silica gel and hexanes/ethyl acetate (1:1) as eluant to yield the title compound as an off-white powder (11.50 g), identified by NMR spectral analyses.

EXAMPLE 4

Preparation of 5-Acetoxy 13β-[(ethoxycarbonyl)oxy]-23-{[(methoxycarbonyl)carbonyl]oxy}-LL-F28249α

A mixture of 5-acetoxy-13β-hydroxy-23-{[(methoxycarbonyl)carbonyl]oxy}-LL-F28249α (0.51 g, 0.67 mmol) in methylene chloride, under nitrogen, is treated with ethyl chloroformate (0.23 g, 2.12 mmol), pyridine (0.25 g, 3.16 mmol) and 4-dimethylaminopyridine (0.05 g, 0.41 mmol) at room temperature. Stirring is continued at room temperature for two hours then the reaction mixture is diluted with ethyl acetate, washed sequentially with water, 5% hydrochloric acid solution, water, 10% sodium bicarbonate solution and brine, dried over anhydrous sodium sulfate and concentrated in vacuo to give a residue. The residue is chromatographed using silica gel and eluted with hexanes/ethyl acetate (3:1) to yield the title compound as a white powder (0.33 g, 59%), identified by $^1$HNMR, $^{13}$CNMR and mass spectral analyses.

EXAMPLE 5

Preparation of 5-Acetoxy-13β-methyl-LL-F28249α

A −78° C. mixture of 5-acetoxy-13β-[(ethoxycarbonyl)oxy]-23-{[(methoxycarbonyl)carbonyl]oxy}-LL-F28249α (0.26 g, 0.31 mmol) in methylene chloride, under nitrogen, is treated over a two minute period with trimethylaluminum (0.46 g, 6.4 mmol). Stirring is continued for 15 minutes at −78° C., then the reaction mixture is warmed to 0° C. and kept at 0° C. with an icebath for 30 minutes, the ice-bath is removed and the reaction mixture is stirred at room temperature for 4 hours.

While cooling with an ice-bath, water (0.5 mL) is slowly added to the reaction mixture. After the gas evolution is complete, the reaction mixture is poured into a mixture of ethyl acetate and 2 normal hydrochloric acid solution. The ethyl acetate layer is separated and washed sequentially with water, 10% sodium bicarbonate solution and brine, dried over anhydrous sodium sulfate and concentrated in vacuo to yield a residue. The residue is chromatographed using silica gel and methylene chloride/acetonitrile (9:1) as eluant to yield the title compound as a white powder (0.144 g, 56%), identified by $^1$HNMR, $^{13}$CNMR and mass spectral analyses.

Following the procedure of Example 5, but substituting triethylaluminum for trimethylaluminum yields 5-acetoxy-13β-ethyl-LL-F28249α.

EXAMPLE 6

Preparation of 5-Acetoxy-13β-methyl-23-oxo-LL-F28249α

To a mixture of 5-acetoxy-13β-methyl-LL-F-28249α (0.188 g, 0.28 mmol), a few 4 angstrom molecular sieves and acetonitrile is added 4-methylmorpholine N-oxide (0.131 g, 1.12 mmol). After stirring for 15 minutes at room temperature tetrapropylammonium perruthenate (0.047 g, 0.13 mmol) is added to the mixture and stirring is continued for one hour. The reaction mixture is filtered through diatomaceous earth, diluted with ethyl acetate and washed sequentially with water, dilute hydrochloric acid solution, water, 10% sodium bicarbonate solution and brine, dried over anhydrous sodium sulfate and concentrated in vacuo to yield a residue. The residue is chromatographed using silica gel and methylene chloride/acetonitrile (19:1) as eluant to yield the title compound as a white powder (0.108 g, 57%), identified by $^1$HNMR, $^{13}$CNMR and mass spectral analyses.

Following the procedure of Example 6, but using 5-acetoxy-13β-ethyl-LL-F28249α for 5-acetoxy-13β-methyl-LL-F28249α yields 5-acetoxy-13β-ethyl-23-oxo-LL-F28249α.

EXAMPLE 7

Preparation of 5-Acetoxy-13β-methyl-23-(O-methyloxime)-LL-F28249α

A mixture of 5-acetoxy-13β-methyl-23-oxo-LL-F28249α (0.144 g, 0.22 mmol), sodium acetate (0.096 g, 1.17 mmol), methoxylamine hydrochloride (0.092 g, 1.1 mmol) and methanol is stirred for one hour at room temperature. The reaction mixture is diluted with ethyl acetate, washed sequentially with water and brine, dried over anhydrous sodium sulfate and concentrated in vacuo to yield a residue. The residue is chromatographed using silica gel and hexanes/ethyl acetate (4:1) as eluant to yield the title compound as a white solid (0.125 g, 83%), identified by $^1$HNMR, $^{13}$CNMR and mass spectral analyses.

Following the procedure of Example 7, substituting 5-acetoxy-13β-ethyl-23-oxo-LL-F28249α for 5-acetoxy-13β-methyl-23-oxo-LL-F28249α yields 5-acetoxy13β-ethyl-23-(O-methyloxime)-LL-F28249α.

EXAMPLE 8

Preparation of 13β-Methyl-23-(O-methyloxime)-LL-F28249α

To a 0° C. solution of 5-acetoxy-13β-methyl-23-(O-methyloxime)-LL-F28249α (0.11 g, 0.16 mmol) and methanol is added sodium hydroxide (0.5 mL, 0.50 mmol). Stirring is continued at 0° C. for two hours, then the reaction mixture is diluted with ethyl acetate, washed sequentially with water and brine, dried over anhydrous sodium sulfate and concentrated in vacuo to yield a residue. The residue is chromatographed using silica gel and hexanes/ethyl acetate (3:1) as eluant to yield the title compound as a white foam (0.079 g, 77%), identified by $^1$HNMR, $^{13}$CNMR and mass spectral analyses.

Following the procedure of Example 8, using 5-acetoxy-13β-ethyl-23-(O-methyloxime)-LL-F28249α in place of 5-acetoxy-13β-methyl-23-(O-methyloxime)-LL-F28249α yields 13β-ethyl-23-(O-methyloxime)-LL-F28249α.

EXAMPLE 9

Evaluation Of The Antiparasitic Activity Of Test Compounds

The antiparasitic activity of the compounds of the present invention at various concentrations of active ingredient is determined by the following test examples. The results of these tests are summarized in Table I.

Evaluation of test compounds for controlling Trichostrongylus colubriformis in warm-blooded animals In these tests the active ingredient is dissolved in polyethylene glycol and dimethylsulfoxide (PEG:DMSO) (1:2 v/v) in sufficient quantity to provide treatments that deliver from 0.0156 to 0.1250 mg/kg of test compound to the animal.

To evaluate the test compounds, 5 week old male gerbils are infected with 400–600 infective *T. colubriformis* larvae of sheep origin on day 0. On day 7, the gerbils are weighed and treatment initiated. Test compounds are administered by gavage on the 7th day after treatment. The gerbils are sacrificed on the 11th day after treatment, and the remaining worms counted. The percent efficacy is calculated by comparing worm counts in treated animals with those from untreated infected controls using the following formula.

$$\frac{\text{Control mean} - \text{treated mean}}{\text{control mean}} \times 100 = \% \text{ Efficacy}$$

Three replicates per treatment are employed in these evaluations.

The data obtained are summarized in Table I.

Evaluation of test compounds for controlling *Psoroptes cuniculi8* (Ear Mites)

On the day prior to test, or the morning of test, test compounds are dissolved in acetone and diluted to the desired concentrations. The concentration should be calculated so that 400 μL contains the amount to be placed on each filter paper. 400 μL of this solution is pipetted onto a top (3.7 cm dia) and bottom (3.5 cm dia) filter paper disc which is then placed on a ceramic plate to dry. [NOTE: This should be done under a hood.] There is a rough and smooth side to the filter paper. The test solution should be applied to the rough side which is placed up while drying. When dry, the two discs are placed in a Petri dish with the rough sides facing in separated by a small piece of stiff paper folded in the shape of a tent. Dishes are held at room temperature overnight, if done the day before the test. A standard at 0.01, 0.1 and 1.0 μL/cm² is run in each test.

Scab (containing mites) is collected from the ears of infested rabbits the morning of the test. This material is placed in a large Petri dish under an illuminated magnifier. Mites crawl out of the scab and are easily collected on the point of a dissecting needle or one prong of a pair of fine forceps. The top filter paper in each dish is removed and 12 mites are placed on the bottom disk and the top paper replaced. Before replacing the top of the Petri dish the rim of the dish is smeared with Vaseline to trap any escaping mites.

For evaluation tests there are generally 4 replicates of each dose which are counted, 2 at 4 hours and 2 at 24 hours.

After mites are added to the dishes, the dishes in each replicate are placed in a tray which is then placed in a plastic bag with several wet towels and held at room temperature.

After 4 or 24 hours, dishes are examined under a dissecting scope as follows

1. Open dish carefully, remove top filter paper and save.
2. Draw a small circle approximately ½ cm in diameter on bottom filter paper using a soft pencil.
3. Using a disposable pipette, gently wet the area in and around the circle.
4. Transfer all mites from the dish into this circle. Look carefully—on cover, top filter paper and under bottom paper for mites.
5. Count and record the number of mites in the circle.
6. Replace the top cover and set the dish aside.
7. A minimum of 15 minutes later, count the mites remaining in the circle (these are dead mites).
8. Calculate and record the number of live mites.
9. Calculate percent efficacy as follows:

$$\frac{\text{Total of Dead mites}}{\text{Total number of mites}} \times 100 = \% \text{ Efficacy}$$

The data obtained are summarized in Table I.

TABLE I

| | Evaluation Of The Antiparasitic Activity Of Test Compounds | | | | | | | |
|---|---|---|---|---|---|---|---|---|
| | T. colubriformis (mg/kg) | | | | P. cuniculi (micrograms/cm²) | | | |
| Test Compound | 0.125 | 0.0625 | 0.0313 | 0.0156 | 4.0 | 1.0 | 0.1 | 0.01 |
| 13beta-Methyl-23-(O-methyloxime)-LL-F28249alpha | 99 | 98 | 53 | 17 | 100 | 98 | 98 | 100 |
| 13beta-Ethyl-23-(O-methyloxime)-LL-F28249alpha | 95 | | | | 91 | | | |

EXAMPLE 10

Evaluation Of The Insecticidal And Acaricidal Activity of Test Compounds

In the following evaluations, test solutions are prepared by dissolving the test compound in a 35% acetone in water mixture to a concentration of 10,000 ppm. Subsequent dilutions are made with water as needed.

*Heliothis virescens*, egg, tobacco budworm

A young cotton leaf about 6–7 cm long is dipped in the test solution with agitation for 3 seconds. Eggs are collected on a cheesecloth and the cheesecloth is cut into 10–20 mm squares containing about 50–100 eggs each (6–30 hours old). A square of cheesecloth with eggs is also dipped in the test solution and placed on the treated leaf. The combination is placed in a hood to dry, then placed in an 8 oz paper cup, into which a 5 cm length of damp dental wick has been placed. A clear plastic lid is put on the top of the cup and the treatments are held for 3 days before mortality counts are made.

*Aphis fabae*, mixed instar, bean aphid

Pots containing single nasturtium plants (Tropaeolum sp.) about 5 cm tall, are infested with about 100–200 aphids 1 day before the test. Each pot is sprayed with the test solution for 2 revolutions of a 4 rpm turn-table in a hood, using a #154 DeVilbiss atomizer. The spray tip is held about 15 cm from the plant, and the spray directed so as to give complete coverage of the plants and the aphids. The sprayed pots are set on their sides on white enamel trays and held for 2 days, following which mortality estimates are made.

*Tetranychus urticae* (P-resistant strain) 2-spotted spider mite

Sieva lima bean plants with primary leaves expanded to 7–8 cm are selected and cut back to one plant per pot. A small piece is cut from a leaf taken from the main colony of mites and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test solution for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

| Rating Scale | |
|---|---|
| 0 = no effect | 5 = 56-65% kill |
| 1 = 10-25% kill | 6 = 66-75% kill |
| 2 = 26-35% kill | 7 = 76-85% kill |
| 3 = 36-45% kill | 8 = 86-99% kill |
| 4 = 46-55% kill | 9 = 100% kill |

The data obtained are summarized in Table II.

TABLE II

Evaluation Of The Insecticidal And Acaricidal Activity Of Test Compounds

| Test Compound | Tobacco Budworm egg (ppm) 100 | Bean Aphid (ppm) 10 | P-resistant Mites (ppm) | | |
|---|---|---|---|---|---|
| | | | 10 | 1 | 0.1 |
| 13beta-Methyl-23-(O-methyloxime)-LL-F28249alpha | 8 | 8 | 9 | 9 | 9 |
| 13beta-Ethyl-23-(O-methyloxime)-LL-F28249alpha | 9 | 9 | 5 | 9 | 8 |

What is claimed is:

1. A compound having the structural formula:

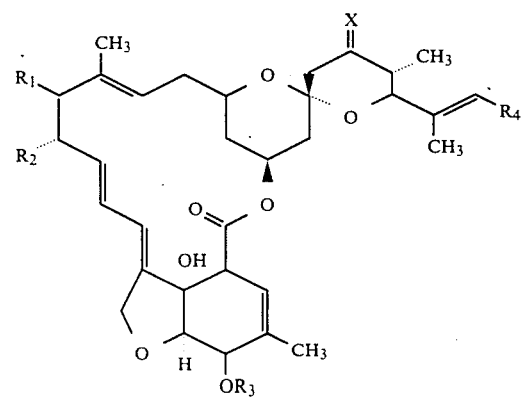

wherein
$R_1$ is $C_1$-$C_4$ alkyl;
$R_2$ is hydrogen, methyl or ethyl;
$R_3$ is hydrogen, $C_1$-$C_4$ alkyl or

$R_5$ is hydrogen, $C_1$-$C_4$ alkyl, $C_1$-$C_4$ haloalkyl, $C_1$-$C_4$ alkoxy, phenoxy, $C_1$-$C_4$ alkoxymethyl, phenoxymethyl, or phenyl optionally substituted with 1 nitro, 1-3 halogens, 1-3 $C_1$-$C_4$ alkyl, or 1-3 $C_1$-$C_4$ alkoxy;
$R_4$ is methyl, ethyl or isopropyl;
X is oxygen, $NOR_6$ or N-$NHR_7$;
$R_6$ is hydrogen, $C_1$-$C_4$ alkyl, $C_1$-$C_4$ alkoxymethyl, $C_1$-$C_4$ alkanoyl, benzyl or phenyl; and
$R_7$ is $C_1$-$C_4$ acyl, $C_1$-$C_4$ alkyl or benzoyl.

2. The compound according to claim 1, wherein
$R_1$ is methyl, ethyl or isopropyl;
$R_2$ is methyl;
$R_3$ is hydrogen, $C_1$-$C_4$ alkyl or

$R_5$ is hydrogen, $C_1$-$C_4$ alkoxymethyl, $C_1$-$C_4$ halomethyl or formyl;
$R_4$ is isopropyl;
X is $NOR_6$; and
$R_6$ is $C_1$-$C_4$ alkyl.

3. The compound according to claim 2, wherein
$R_1$ is methyl;
$R_3$ is hydrogen; and
$R_6$ is methyl.

4. The compound according to claim 2, wherein
$R_1$ is ethyl;
$R_3$ is hydrogen; and $R_6$ is methyl.

5. A composition for controlling endo- and ectoparasites, insects, acarids and nematodes comprising an agronomically acceptable carrier containing a prophylactically, therapeutically, pharmaceutically or insecticidally effective amount of the compound of claim 1.

6. A method for treating, controlling and protecting a warm-blooded animal from infestation and infection by endo- and ectoparasites which comprises administering to said animal an endo- or ectoparasiticidally effective amount of the compound of claim 1.

7. The method according to claim 6, wherein the compound has the structural formula as described in claim 1 and
$R_1$ is methyl, ethyl or isopropyl;
$R_2$ is methyl;
$R_3$ is hydrogen, $C_1$-$C_4$ alkyl, or

$R_5$ is hydrogen, $C_1$-$C_4$ alkoxymethyl, $C_1$-$C_4$ halomethyl or formyl;
$R_4$ is isopropyl;
X is $NOR_6$; and
$R_6$ is $C_1$-$C_4$ alkyl.

8. A method for protecting crops, trees, shrubs, stored grain and ornamental plants from damage by an insects, acarids or nematodes which comprises applying to said crops, trees, shrubs, stored grain or ornamental plants an insecticidally, acaricidally or nematicidally effective amount of the compound of claim 1.

9. The method according to claim 8, wherein the compound has the structural formula as described in claim 1 and $R_1$ is methyl, ethyl or isopropyl;
$R_2$ is methyl;
$R_3$ is hydrogen, $C_1$–$C_4$ alkyl, or
$R_5$ is hydrogen, $C_1$–$C_4$ alkoxymethyl, $C_1$–$C_4$ halomethyl or formyl;
$R_4$ is isopropyl;
X is $NOR_6$; and
$R_6$ is $C_1$–$C_4$ alkyl.
* * * * *